US009817010B2

(12) United States Patent
Blouin et al.

(10) Patent No.: US 9,817,010 B2
(45) Date of Patent: *Nov. 14, 2017

(54) TELESCOPING CLOSED-TUBE SAMPLING ASSEMBLY

(71) Applicant: INSTRUMENTATION LABORATORY COMPANY, Bedford, MA (US)

(72) Inventors: Matthew Blouin, Townsend, MA (US); Gregory Murphy, Lowell, MA (US); Diana Mackenzie, Waltham, MA (US); Alan Weeks, S. Eaton, MA (US); Daniel Kobrenski, North Andover, MA (US)

(73) Assignee: Instrumentation Laboratory Company, Bedford, MA (US)

( * ) Notice: Subject to any disclaimer, the term of this patent is extended or adjusted under 35 U.S.C. 154(b) by 577 days.

This patent is subject to a terminal disclaimer.

(21) Appl. No.: 14/272,649

(22) Filed: May 8, 2014

(65) Prior Publication Data

US 2014/0302610 A1  Oct. 9, 2014

Related U.S. Application Data

(63) Continuation of application No. 11/417,770, filed on May 4, 2006, now Pat. No. 8,758,702.
(Continued)

(51) Int. Cl.
*G01N 35/02* (2006.01)
*B01L 3/02* (2006.01)
(Continued)

(52) U.S. Cl.
CPC ............ *G01N 35/026* (2013.01); *B01L 3/021* (2013.01); *B01L 99/00* (2013.01);
(Continued)

(58) Field of Classification Search
CPC ............ B01L 3/021; B01L 2300/0672; B01L 2400/0487; B01L 99/00; G01N 35/1004;
(Continued)

(56) References Cited

U.S. PATENT DOCUMENTS 4,495,149 A  1/1985 Iwata et al.
4,577,514 A  3/1986 Bradley et al.
(Continued)

FOREIGN PATENT DOCUMENTS

DE  30 39 475  5/1982
DE  32 34 563  5/1983
(Continued)

OTHER PUBLICATIONS

Office Action dated Sep. 9, 2016 in corresponding European Application No. 06759079.4, filed May 4, 2006, (7 pages).
(Continued)

*Primary Examiner* — Shogo Sasaki
(74) *Attorney, Agent, or Firm* — Burns & Levinson, LLP

(57) ABSTRACT

A clinical diagnostic sample analyzer for analyzing a sample of a patient is disclosed. The analyzer includes a telescoping closed-tube sampling assembly with a sample probe concentrically housed within a piercing probe and a venting mechanism. The closed-tube sampling assembly is used for aspirating a sample from a sample tube for analysis by a clinical diagnostic sample analyzer.

13 Claims, 10 Drawing Sheets

Related U.S. Application Data

(60) Provisional application No. 60/678,615, filed on May 6, 2005, provisional application No. 60/678,597, filed on May 6, 2005.

(51) Int. Cl.
  *G01N 35/10* (2006.01)
  *B01L 99/00* (2010.01)

(52) U.S. Cl.
  CPC ..... *G01N 35/1004* (2013.01); *G01N 35/1011* (2013.01); *G01N 35/1079* (2013.01); *B01L 2300/0672* (2013.01); *B01L 2400/0487* (2013.01); *G01N 2035/1006* (2013.01); *Y10T 436/114998* (2015.01); *Y10T 436/2575* (2015.01)

(58) Field of Classification Search
  CPC ........... G01N 35/1011; G01N 35/1079; G01N 35/026; G01N 2035/1006; Y10T 436/114998; Y10T 436/2575
  USPC ... 422/63, 67, 500, 501, 509–513, 515–519, 422/521–527, 534, 535, 106, 107; 436/49
  See application file for complete search history.

(56) References Cited

U.S. PATENT DOCUMENTS

| | | |
|---|---|---|
| 4,588,394 A | 5/1986 | Schulte et al. |
| 4,624,148 A | 11/1986 | Averette |
| 4,713,974 A | 12/1987 | Stone |
| 4,768,568 A | 9/1988 | Fournier et al. |
| 4,788,871 A | 12/1988 | Nelson et al. |
| 4,811,611 A | 3/1989 | Uffenheimer |
| 4,865,090 A | 9/1989 | Burolla et al. |
| 4,888,004 A | 12/1989 | Williamson, IV et al. |
| 4,921,491 A | 5/1990 | Champ |
| 4,951,512 A | 8/1990 | Mazza et al. |
| 4,974,457 A | 12/1990 | Angst et al. |
| 4,982,769 A | 1/1991 | Fournier et al. |
| 5,147,551 A | 9/1992 | Averette |
| 5,163,909 A | 11/1992 | Stewart |
| 5,215,217 A | 6/1993 | Leslie |
| 5,220,947 A | 6/1993 | Cauquil et al. |
| 5,248,480 A | 9/1993 | Greenfield et al. |
| 5,262,049 A | 11/1993 | Ferkany |
| 5,286,453 A | 2/1994 | Pope |
| 5,339,701 A | 8/1994 | Green |
| 5,340,541 A | 8/1994 | Jackson et al. |
| 5,353,652 A | 10/1994 | Houck |
| 5,354,537 A | 10/1994 | Moreno |
| 5,481,852 A | 1/1996 | Mitchell |
| 5,558,838 A | 9/1996 | Uffenheimer |
| 5,578,495 A | 11/1996 | Wilks |
| 5,653,686 A | 8/1997 | Coulter et al. |
| 5,755,696 A | 5/1998 | Caizza |
| 5,935,523 A | 8/1999 | McCandless et al. |
| 5,945,070 A | 8/1999 | Kath et al. |
| 5,976,468 A | 11/1999 | Godec et al. |
| 5,993,744 A | 11/1999 | Rao et al. |
| 5,998,217 A | 12/1999 | Rao et al. |
| 6,040,186 A | 3/2000 | Lewis et al. |
| 6,056,921 A | 5/2000 | Rao et al. |
| 6,109,480 A | 8/2000 | Monsrud et al. |
| 6,126,903 A | 10/2000 | Preston et al. |
| 6,143,573 A | 11/2000 | Rao et al. |
| 6,162,197 A | 12/2000 | Mohammad |
| 6,209,738 B1 | 4/2001 | Jansen et al. |
| H1960 H | 6/2001 | Conrad et al. |
| 6,269,846 B1 | 8/2001 | Overbeck et al. |
| 6,274,087 B1 | 8/2001 | Preston et al. |
| 6,284,549 B1 | 9/2001 | Guthrie |
| 6,286,375 B1 | 9/2001 | Ward |
| 6,301,959 B1 | 10/2001 | Hrametz et al. |
| 6,302,870 B1 | 10/2001 | Jacobsen et al. |
| 6,322,752 B1 | 11/2001 | Siddiqui et al. |
| 6,332,871 B1 | 12/2001 | Douglas et al. |
| 6,360,794 B1 | 3/2002 | Turner |
| 6,405,609 B1 | 6/2002 | Richards et al. |
| 6,428,519 B1 | 8/2002 | Arnissolle |
| RE37,908 E | 11/2002 | Kinsey |
| 6,503,453 B1 | 1/2003 | Sagstetter |
| 6,524,276 B1 | 2/2003 | Halseth et al. |
| 6,524,278 B1 | 2/2003 | Campbell et al. |
| 6,557,428 B2 | 5/2003 | Wickland et al. |
| 6,616,637 B2 | 9/2003 | Alexander et al. |
| 6,626,885 B2 | 9/2003 | Massengale |
| 6,627,156 B2 | 9/2003 | Goodale et al. |
| 6,641,555 B1 | 11/2003 | Botich et al. |
| 6,648,835 B1 | 11/2003 | Shemesh |
| 6,656,433 B2 | 12/2003 | Sasso |
| 6,659,177 B2 | 12/2003 | Bolze et al. |
| 6,682,504 B2 | 1/2004 | Nelson et al. |
| 6,694,197 B1 | 2/2004 | Hatcher et al. |
| 6,727,101 B1 | 4/2004 | Sagstetter |
| 6,746,429 B2 | 6/2004 | Sadowski et al. |
| 6,759,014 B2 | 7/2004 | Dales et al. |
| 6,805,170 B2 | 10/2004 | Py |
| 6,919,044 B1 | 7/2005 | Shibata et al. |
| 6,921,391 B1 | 7/2005 | Barker et al. |
| 6,935,199 B2 | 8/2005 | Wickland et al. |
| 6,939,319 B1 | 9/2005 | Anstead et al. |
| 6,945,129 B2 | 9/2005 | Escal |
| 6,948,391 B2 | 9/2005 | Brassell et al. |
| 6,997,916 B2 | 2/2006 | Simas, Jr. et al. |
| 2001/0021354 A1 | 9/2001 | Lang |
| 2003/0032173 A1 | 2/2003 | Farina et al. |
| 2003/0054360 A1 | 3/2003 | Gold et al. |
| 2003/0054740 A1 | 3/2003 | Mansky |
| 2003/0155034 A1 | 8/2003 | De Beukeleer et al. |
| 2005/0223822 A1 | 10/2005 | Ozbal |
| 2006/0263250 A1 | 11/2006 | Blouin et al. |

FOREIGN PATENT DOCUMENTS

| | | |
|---|---|---|
| DE | 102 07 499 | 9/2003 |
| DE | 10207499 | 9/2003 |
| EP | 0 884 575 | 12/1998 |
| EP | 1 118 861 | 7/2001 |
| JP | 62-182665 | 8/1987 |
| JP | 62242858 | 10/1987 |
| JP | 63-160943 | 7/1988 |
| JP | 06-201667 | 7/1994 |
| JP | 09-015113 | 1/1997 |
| JP | 09-054023 | 2/1997 |
| JP | 10-123025 | 5/1998 |
| WO | WO95/06867 | 3/1995 |
| WO | 99/36760 | 7/1999 |
| WO | WO01/58593 | 8/2001 |
| WO | WO2005/100945 | 10/2005 |

OTHER PUBLICATIONS

International Search Report for International Application No. PCT/US2006/017238, dated Nov. 17, 2006 (7 pages).*
Written Opinion for international Application No. PCT/US2006/017238, dated Nov. 17, 2006.*
English translation of an Office action issued in a counterpart Japanese patent application No. 2008510223 dated Feb. 28, 2014 (4 pages).*, JP 2012-265432

TELESCOPING CLOSED-TUBE SAMPLING ASSEMBLY

CROSS REFERENCE TO RELATED APPLICATION

This application is a continuation application of a application Ser. No. 11/417,770, filed on May 4, 2006, now granted U.S. Pat. No. 8,758,702 issued on Jun. 24, 2014, which claims priority to and benefit of U.S. Provisional Applications 60/678,615, filed May 6, 2005 and 60/678,597, filed on May 6, 2005, the entire content of each application is incorporated herein by reference.

FIELD OF THE INVENTION

The invention relates to a clinical diagnostic analyzer for analyzing fluid samples such as patient blood samples. More particularly, the invention relates to a closed tube sample collecting device including a piercing probe and sample probe assembly mounted on a clinical diagnostic analyzer for accessing a fluid in vial, venting mechanisms associated with the closed tube sample collecting device, and methods for sampling and clearing a closed tube sample collecting device between patient samples to prevent cross contamination of the blood samples.

BACKGROUND OF THE INVENTION

Blood and other bodily fluids handled in large quantities by medical laboratories for processing and testing present cost containment and biohazard issues for the laboratory. In order to minimize costs of testing fluids, the equipment and procedures utilized to process such samples are becoming increasingly automated so as to permit the procedures to be performed as quickly as possible with minimum labor. Automating sample processing has the additional benefit of minimizing the handling of blood and other bodily fluids that are now classified as hazardous substances.

In order to analyze samples of patient fluids, including human blood, a sample must first be taken from the patient. Usually the sample is housed within a container to be aspirated from during analyzer operation. These sample containers are then loaded into an automatic sample analyzer. If the sample container is capped, the cap must first be removed before a sample can be aspirated for analysis. This can be done manually by the operator, or, if the sample container has a frangible seal, the analyzer may contain a piercing apparatus to break the seal on the container to allow aspiration of a fluid sample.

Currently available commercial sample analyzers capable of piercing sealed containers have several disadvantages that reduce the effectiveness and efficiency of the sampling and analysis operations. For example, some analyzers use the sample aspirator in a dual mode to break the frangible seal, as well as to aspirate sample. The use of the sample aspirator in the dual mode may cause blockage of the sample aspirator if fragments of the seal enter the tip of the aspirator or the venting apertures disposed on the sample aspirator. Additionally, even if a separate piercing apparatus is used to break the frangible seal, when the sample aspirator alone subsequently enters the perforated seal, debris from the seal can block the sample aspirator tip and/or any venting ports disposed thereon, thus reducing the accuracy of the sample volume aspirated, and potentially damaging the sample aspirator. Clogged venting ports and aspirator tips increase the risk of cross-contamination of patient samples and also require that more time be dedicated to cleaning of the apparatus, thus increasing throughput times and decreasing the effectiveness of the analyzer.

Furthermore, some analyzers use a piercing device that is separated from the sampling device. In some devices, the piercing device is located in close proximity to the sampling device; however, in some devices the piercing device and sampling device may be located in different areas of the analyzer. Consequently, additional time is required to first position the sample tube for piercing and to then either reposition the sample in relation to the sample aspirator, or to move the sample aspirator to the location of the sample vial. These movements increase the throughput time of the sample analyzer, thus decreasing its efficiency.

In addition, currently available sample analyzers may only be able to aspirate sample from one type of vial or sample container at a time. Consequently, if an operator had multiple samples in different sized vials, only similar containers could be processed in the same batch. A new cycle or additional analyzer calibration would be required for each style of vial present. The inability of a sample analyzer to process different sized vials in the same batch negatively affects the throughput time of the analyzer, decreasing its efficiency.

There is, therefore, a demonstrated need in the art for a more efficient automated sample analyzer with improved throughput rates and improved probe designs. The improved sample analyzer reduces or eliminates the problems associated with current devices used to pierce sample vial caps, reduces clogging of both the piercing and sampling mechanisms thereby reducing cross-contamination, improving the accuracy of aspirating sample volumes, and improves access to samples in a variety of differently sized sample tubes.

SUMMARY OF THE INVENTION

The present invention provides a clinical diagnostic analyzer comprising an assembly for obtaining a sample of fluid from a fluid sample tube or vial. The invention also provides a method for sampling fluid from a fluid sample tube or vial.

In one aspect, the invention provides a clinical diagnostic analyzer comprising a sample collecting device for sampling fluid in a container. In one embodiment, the device includes a first tube comprising a lumen and a piercing end, a second tube comprising a lumen and a free end, and a valve operatively joined to the piercing tube, the valve comprising an open position and a closed position, and a positive pressure gas source for generating positive gas pressure operatively joined to the valve. The positive gas pressure generated by the positive pressure gas source purges the piercing tube lumen when the valve is in the open position. The second tube is at least partially housed within the lumen of the first tube and the free end of the second tube transitions from an enclosed position within the lumen of the first tube to a deployed position beyond the piercing end of the first tube. At least one of the first or the second tube axially moves relative to the other. The second tube samples fluid in the container when the free end of the second tube is deployed relative to the piercing end of the first tube.

In one embodiment, the first tube and the second tube move simultaneously with one another, while in another embodiment, the second tube is stationary and the first tube moves relative to the second tube. In yet another embodiment, the first tube is stationary while the second tube moves relative to the first tube.

In another embodiment, the second tube is coupled to an assembly for passing a gas, e.g., air through the lumen of the second tube, while in yet another embodiment, the first tube is coupled to an assembly for passing a cleaning solution through the lumen of the first tube.

In another embodiment, the apparatus includes a mechanism for triggering the apparatus to pierce the cap of and sample from a sample tube. The mechanism includes a sensor system and an activating member that triggers the apparatus when the member contacts the sample tube. The member may be a foot assembly.

In a further embodiment, the piercing end of the first tube is cut on an angle to reveal an elliptical cross section. The end is beveled.

In another embodiment, the apparatus is coupled to a first carriage assembly to permit movement of the apparatus in a first axis of the analyzer, while in a further embodiment, the first carriage assembly is coupled to a second carriage assembly to permit movement of the apparatus in a second axis of the analyzer. The analyzer may also comprise at least one motor and a computer. In another embodiment, the apparatus further comprises an information processing unit for receiving and sending information to a computer.

In another embodiment of the invention, the first tube may be coupled to a spring-loaded assembly.

According to another embodiment of the invention, the valve of the device is a two-way valve. The device may include one, two, or more two-way valves arranged in series or in parallel. According to another embodiment, the first valve is operatively joined to the positive pressure gas source and the second valve is operatively joined to room air at atmospheric pressure. According to an alternative embodiment, the valve is a three-way valve and the three way valve is operatively joined to the piercing tube, to the positive pressure gas source, and to room air at atmospheric pressure.

According to another embodiment of the invention, the sample collecting device further includes an accumulator. The accumulator is operatively joined to the valve and to the positive pressure gas source. The accumulator is pressurized from about 25 PSIA to 30 PSIA; preferably 27 PSIA. According to another embodiment, the device further includes a gas pressure sensor. The gas pressure sensor is operatively joined to the positive pressure gas source.

In another embodiment, the present invention provides a clinical diagnostic analyzer including an apparatus for sampling fluid in a container. The apparatus includes a first non-perforated tube reciprocally movable in a vertical axis comprising a lumen, a piercing end and another end in communication with a conduit, and a second non-perforated tube comprising a lumen and a free end. The second tube is inseparable during sampling from, and is at least partially housed within the lumen of the first tube. The free end of the second tube transitions from an enclosed position within the lumen of the first tube to a deployed position beyond the piercing end of the first tube. In one embodiment, the first tube moves axially relative to the second tube. In another embodiment the second tube moves axially relative to the first tube or alternatively, both tubes move axially relative to each other. The second tube samples fluid in the container when the free end of the second tube is deployed relative to the piercing end of the first tube.

In one embodiment according to the invention, the piercing end of the first tube may be for example, beveled, cut at an angle to reveal an elliptical cross section, chamfered, or the inner edges of the free end may be rounded.

In one embodiment, the clinical diagnostic analyzer according to the invention includes a spring operatively joined to the first tube to effect movement of the first tube.

The first tube may further feature one or more detents for positioning the first tube in its vertical axis. In a particular embodiment, the analyzer includes a sensor system that engages a member contacting the sample tube to determine when a sample tube is in position for piercing and sampling. The member may be, for example, a foot assembly comprising a through hole.

In one embodiment, the apparatus of the clinical diagnostic analyzer is coupled to a first carriage assembly to permit movement of the apparatus in a first axis of the analyzer. In another embodiment, the first carriage assembly is coupled to a second carriage assembly to permit movement of said apparatus in a second axis of said analyzer.

In one embodiment the clinical diagnostic analyzer according to the invention includes a washing station. The washing station may include a washing container, a radial rinser, a filter, and/or a gas jet, or any combination of the above. In one embodiment the filter is disposed in the lumen of the washing container. The radial rinser features a plurality of radially arranged rinser ports. The apparatus according to the invention may further include an air purge system comprising a tube with an orifice positioned adjacent the tip of the first tube, the air purge system operatively joined to a gas source In another embodiment, the clinical diagnostic analyzer includes a pressurized gas source in communication with the lumen of the first tube for purging residual fluid in the lumen. In yet another embodiment, the clinical diagnostic analyzer features a second tube coupled to an assembly for passing fluid through the lumen of the second tube.

In one embodiment of the invention, the first tube is operatively joined to a sensor to detect contact of the first tube with a fluid or a solid. Alternatively, the second tube is operatively joined to a sensor to detect contact of the second tube with a fluid or a solid. In yet another embodiment the first tube and the second tube are joined by a circuit to prevent signal of false detection of the other tube.

Other aspects of the present invention will be apparent to these skilled in the art upon reading the following description and claims. While the description and drawings are of a particular embodiment, other embodiments fall within the scope of the invention.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF THE INVENTION

The present invention is related to a telescoping piercing probe and sample probe assembly and a venting mechanism mounted on a clinical diagnostic analyzer for automated piercing and sampling of fluid in a vial. The assembly includes a sample probe housed within a piercing probe. All of the following embodiments of the invention include features that improve the efficiency and effectiveness of an automated diagnostic sample analyzer including the piercing probe and sample probe assembly, and the venting mechanism of the invention.

Figure 1:
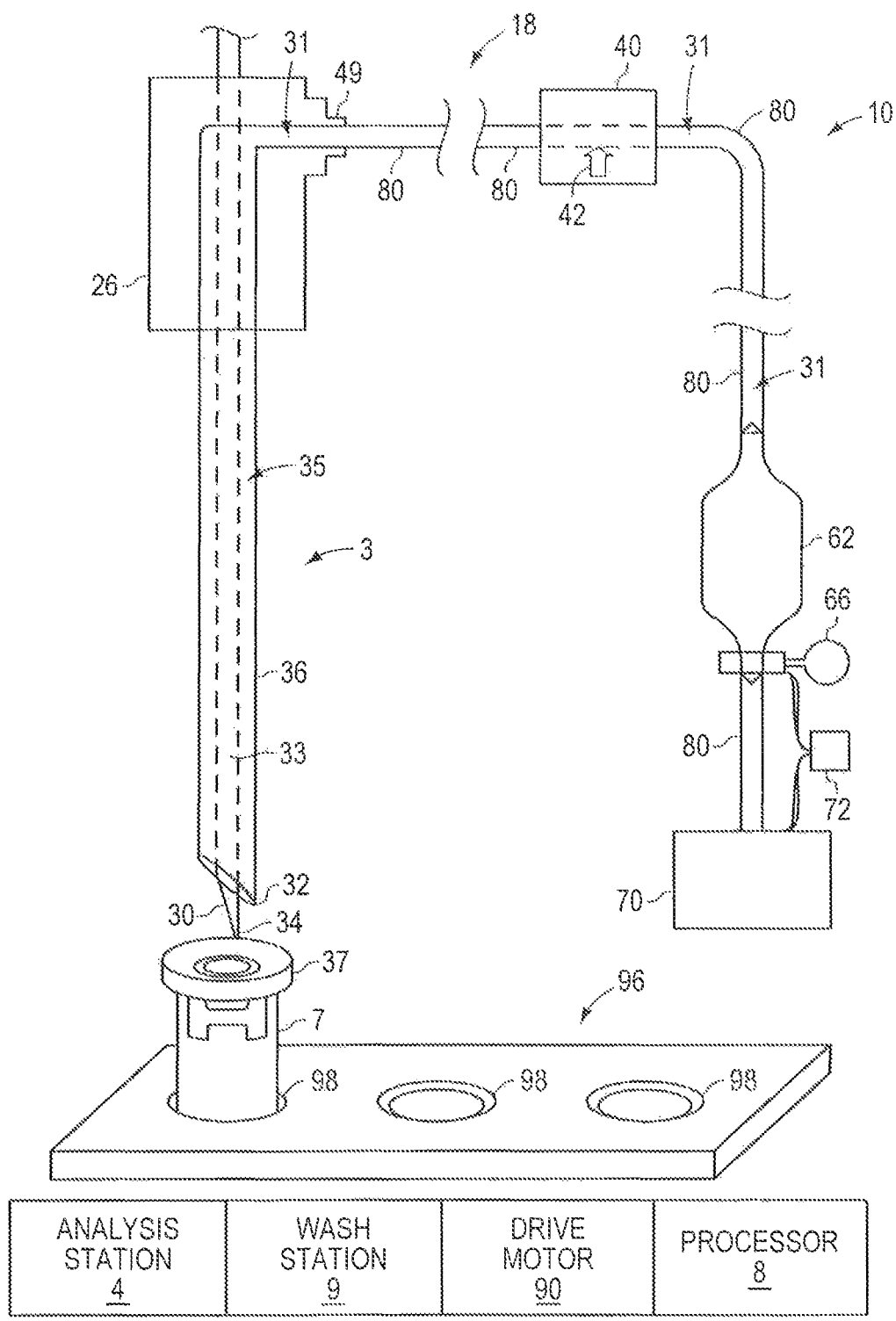
FIG. 1 is a schematic view of a clinical diagnostic analyzer including a sample collecting device according to an illustrative embodiment of the invention.

Referring to FIG. 1, a sample collecting device 18, for example, a closed tube sample collecting device, is a component of an automated clinical diagnostic analyzer 10 that analyzes patient blood samples. The clinical diagnostic analyzer 10 may further include an analysis station 4, a wash station 9, a processor 8, a drive motor 90 and a sample tube rack 96. The sample tube rack 96 includes a plurality of sample tube wells 98. A patient blood sample, contained within a sample tube 7, rests within a sample tube well 98. It is contemplated that the sample collecting device 18 may collect samples from a variety of sized and shaped sample tubes 7, including both closed sample tubes 7, cups (not shown), vials (not shown), and open sample tubes. The closed sample tubes 7 include a sample tube cap or seal 37 to seal the sample from the atmosphere and particulate debris.

Referring still to FIG. 1, in one embodiment according to the invention the sample collecting device 18 includes a sampling assembly 3 comprising a piercing tube 36 comprising an axially-disposed lumen 35, and a sample aspirating probe 30 including an axially disposed lumen 33. In a further embodiment, the sample collecting device 18 may also include one or more valves 40, an accumulator 62, and a positive pressure gas source 70.

Figure 2A:
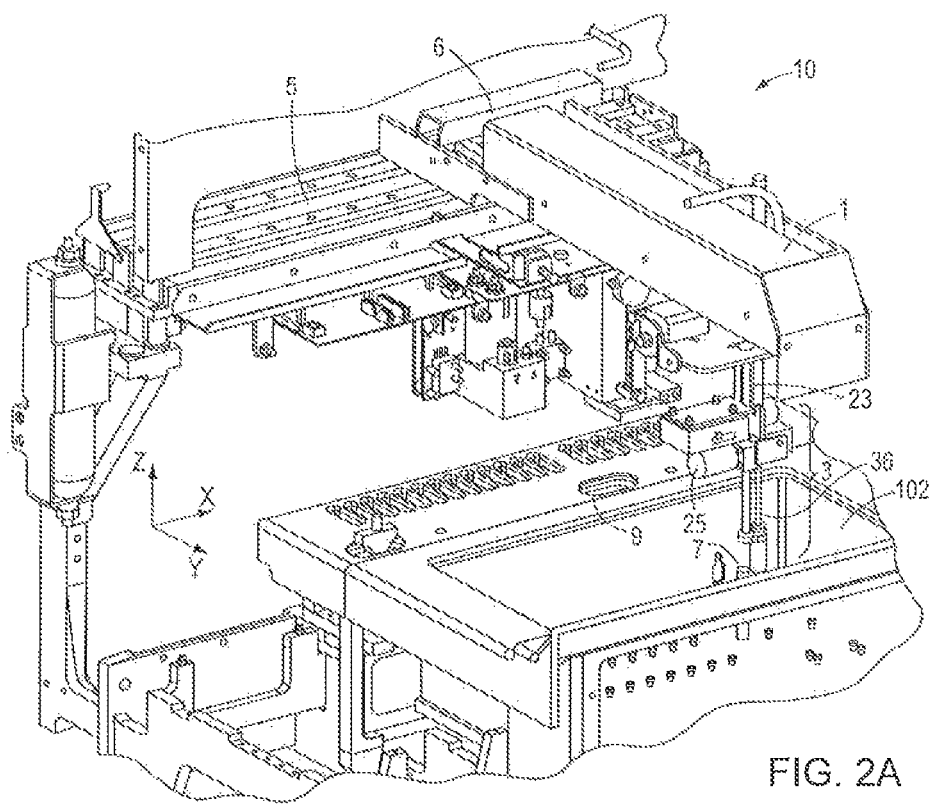
FIG. 2A is a front perspective view of an exemplary closed-tube sampling assembly of the invention housed within a clinical diagnostic sample analyzer.

With reference to FIG. 2A, in one embodiment, the sampling assembly 3 is mounted to a carriage assembly which travels via a bearing rail 5 of an arm 1. The arm 1 is also attached to a second carriage assembly which travels on a second bearing rail (not shown).

With continued reference to FIG. 2A, in one embodiment according to the invention, a cuvette dispenser (not shown) is positioned at the rear of the analyzer 10 to dispense cuvettes (not shown) that receive the sample obtained by the sampling assembly 3. The cuvettes are transported by a tube transport mechanism (not shown) to the analysis station 4 such as, for example, a luminometer.

Figure 2B:
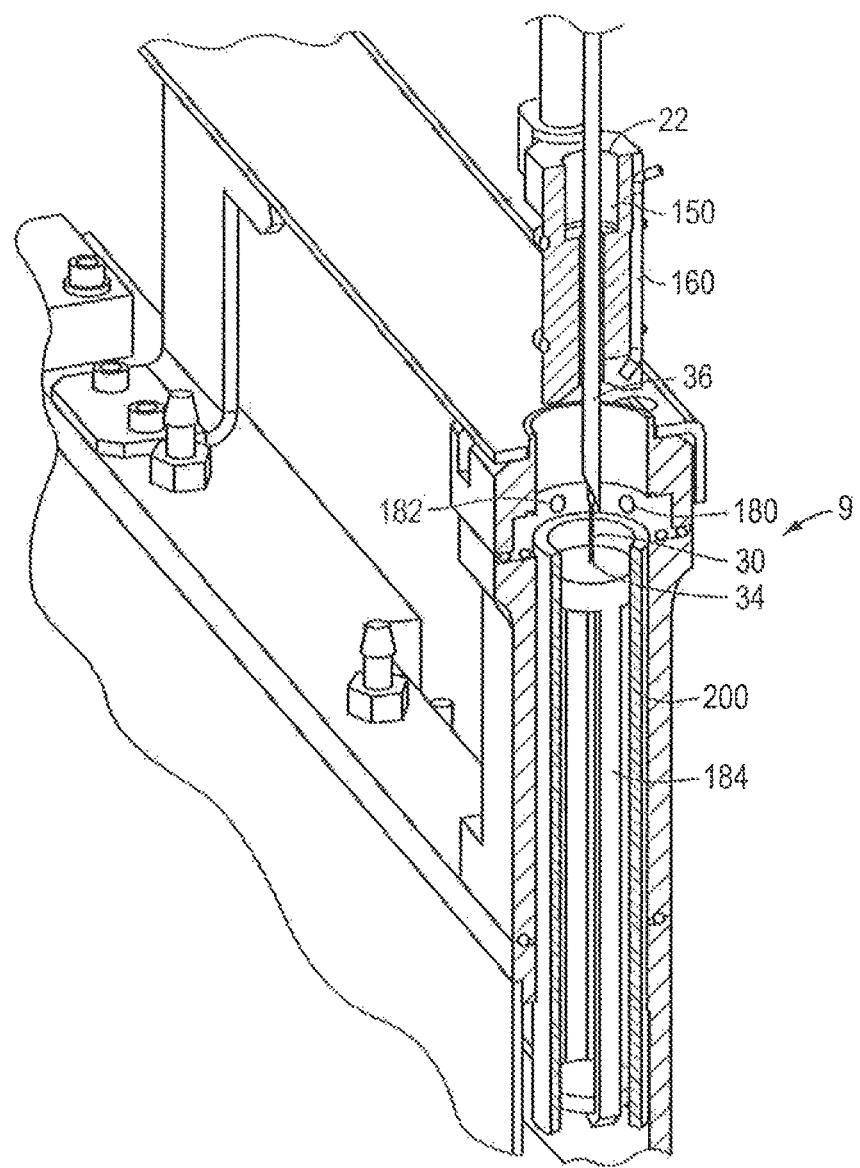
FIG. 2B is a side, partial cutaway view of the washing station shown in FIG. 2A according to the invention.

Referring to FIG. 2B, a further embodiment of the analyzer 10 according to the invention includes a washing station 9. The washing station 9 cleans the piercing probe 36 and sample probe 30 of the sampling assembly 3 after the sample removed from the sample tube 7 is dispensed into a cuvette (not shown). In one embodiment of the invention, the washing station 9 includes a container 200 of washing fluid and a spray device, e.g., a shower 180 that sprays a washing fluid directed to the contaminated piercing probe 36 and/or sample probe 30. In another embodiment, the washing station 9 further includes a filter 184 for removing debris. The filter 184 may be substantially cylindrical, disc-shaped or conical. In a particular embodiment the filter is cylindrical and disposed in the lumen of the washing container. In yet another embodiment, the washing station 9 includes a jet 160 connected to a gas source (not shown) for directing a blast of drying gas to the distal end of the piercing probe to dry the probe.

Referring again to FIG. 2A, a computer (not shown) controls the overall activity of the analyzer 10 by receiving input from the various sensors and information processing units of the analyzer 10 and directing the movement of the various parts of the analyzer 10, such as the movement of the positioning arm 1 along the rail 5, according to one embodiment of the invention. The movement of the positioning arm 1 is driven by a motor 90. There may also be additional motors to drive movement of other parts of the analyzer 10. The clinical diagnostic sample analyzer 10 shown here is only one example of an analyzer utilizing the sampling assembly 3 of the invention. The sampling assembly 3 may be used according to the invention with any appropriately configured clinical diagnostic sample analyzer.

Figures 3, 5:
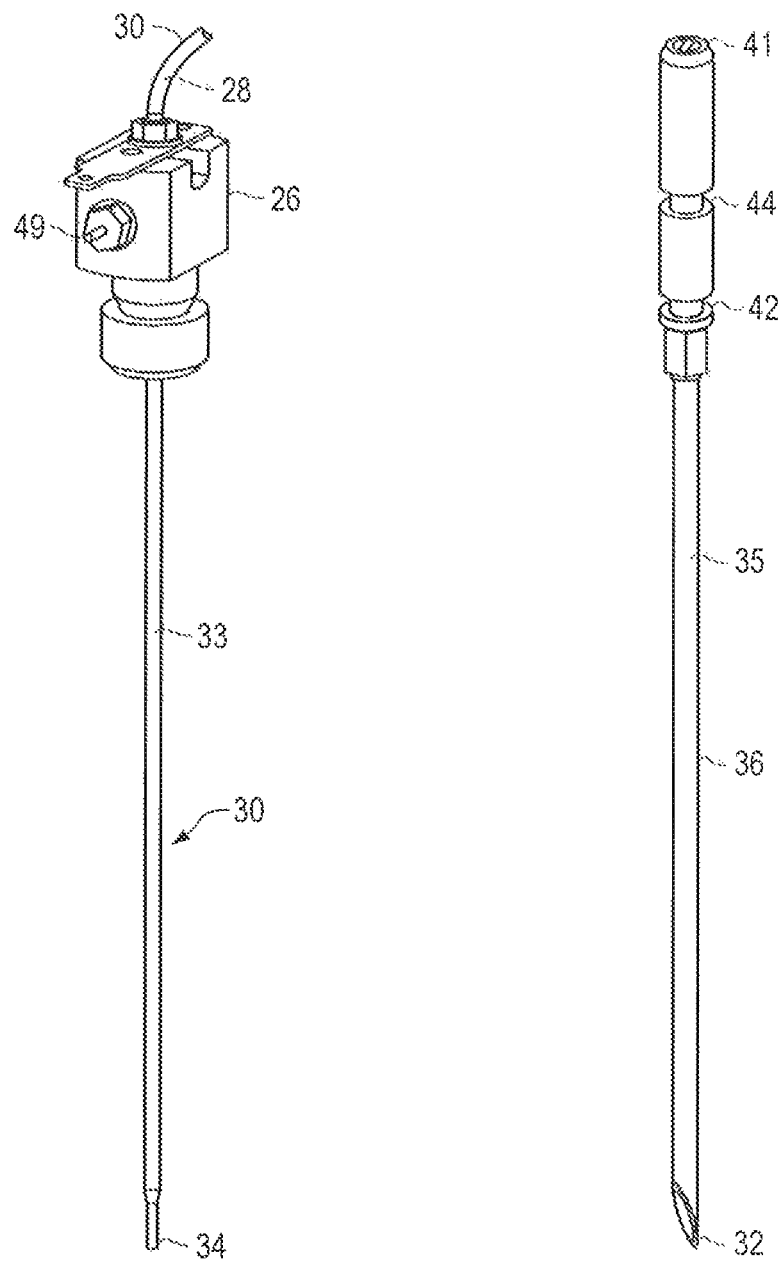
FIG. 3 depicts an exemplary piercing probe of the invention.
FIG. 5 depicts an exemplary sample probe of the invention.

FIG. 3 depicts an exemplary piercing probe 36 of the invention. The piercing probe 36 is a tubular structure including a distal end, a proximal end, and an axially disposed lumen 35 that opens on the distal and proximal end of the tubular structure. The walls of the tubular structure are non-perforated; i.e., without holes, ports or vents. In one embodiment, the piercing probe 36 is reciprocally movable in a vertical axis.

According to another embodiment, a tip 32 for piercing a sample tube 7 is disposed at the distal end of the piercing probe 36, while the piercing probe 36 proximal to the tip 32 has at least a first detent 42 and a second detent 44 proximal to the first detent 42. Additional detents may also be included in the probe 36 according to alternative embodiments of the invention. According to a particular embodiment, the piercing probe 36 includes only one detent (not shown). The first and second detents assist in positioning the piercing probe 36 relative to the sample probe 30 and will be discussed further below. The proximal end of the piercing probe 36 also may be in communication with a conduit.

Figure 4A:
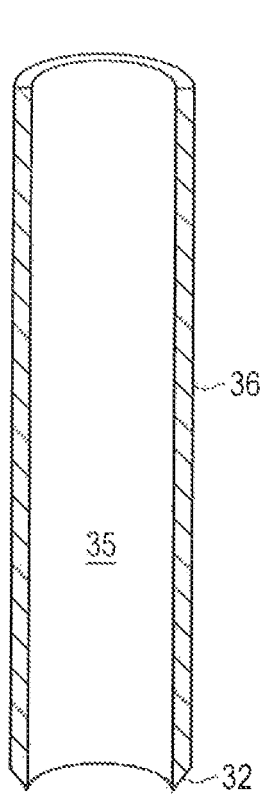
FIG. 4A shows a cutaway view of a portion of an exemplary piercing probe including a blunt tip and chamfered edge.
Figure 4B:
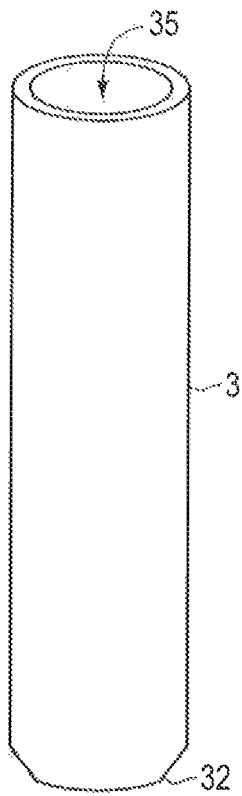
FIG. 4B shows a side view of the portion of the exemplary piercing probe of FIG. 4A.
Figure 4C:
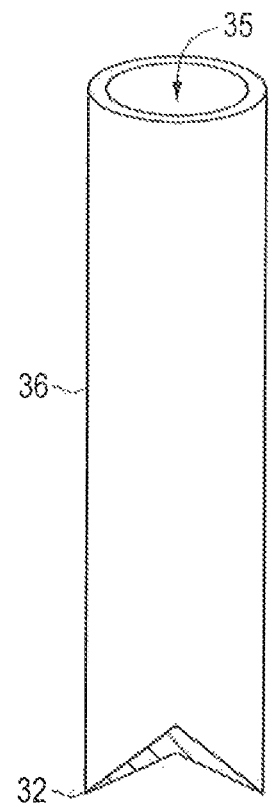
FIG. 4C shows a side view of a portion of an exemplary piercing probe with a double-pointed tip 32.

While in one embodiment of the invention, the tip 32 of the piercing probe 36 shown in FIG. 3 is beveled and reveals an elliptical cross-section, the tip 32 may be cut at any angle. As shown in FIGS. 4A-C, the tip may also be one of a variety of different shapes, e.g., diamond, circular, oval, rectangular, toothed and scalloped, for example. FIG. 4A shows a cutaway view of the distal portion of an exemplary piercing probe 36 including a blunt tip 32 that includes a chamfered edge according to one embodiment of the invention. FIG. 4B shows a side view of the portion of the exemplary piercing probe illustrated in FIG. 4A. In another embodiment, FIG. 4C shows a side view of the distal portion of a piercing probe 36 is a double-pointed tip 32. In yet another embodiment, the tip 32 of the piercing probe 36 has multiple points. In another embodiment, the internal edges of the tip 32 of the piercing tube 36 are rounded (not shown). In one further embodiment, the tip 32 of the piercing probe 36 reduces coring of the sample tube cap 37, thus the end surface of the tube may have one or more cuts or be sharpened to reduce coring. Any configuration of tip 32 capable of perforating a seal 37 of a sample tube 7 may be used.

FIG. 5 depicts an exemplary sample probe 30 of the invention. The sample probe 30 is a tubular structure including an axially disposed lumen, a proximal end 28, and a distal free end 34. The sample probe 30 is axially disposed in and inseparable from the lumen 35 of the piercing probe 36 during the sampling step. The lumen 34 of the sample probe 30 opens at the distal and proximal end of the tubular structure. The walls of the tubular structure of the sample probe 30 are non-perforated, i.e., without holes, ports or vents. The free end 34 includes an opening for fluid communication between the probe lumen 33 and the exterior of the probe 30. The free end 34 of the probe is inserted into a sample to aspirate a sample from a sample vial 7. In one embodiment, the proximal end 28 of the sample probe 30 is coupled to a seal assembly 26 which will be discussed in detail below. The proximal end 28 of the sample probe 30 is connectable to a supply tube or other supply member that may serve as a conduit for the introduction of fluids or gases for cleaning or rinsing the lumen 33 of the sample probe 30 or for transport of fluid by the sample probe 30, for example, to or from a sample tube 7.

Figure 6:
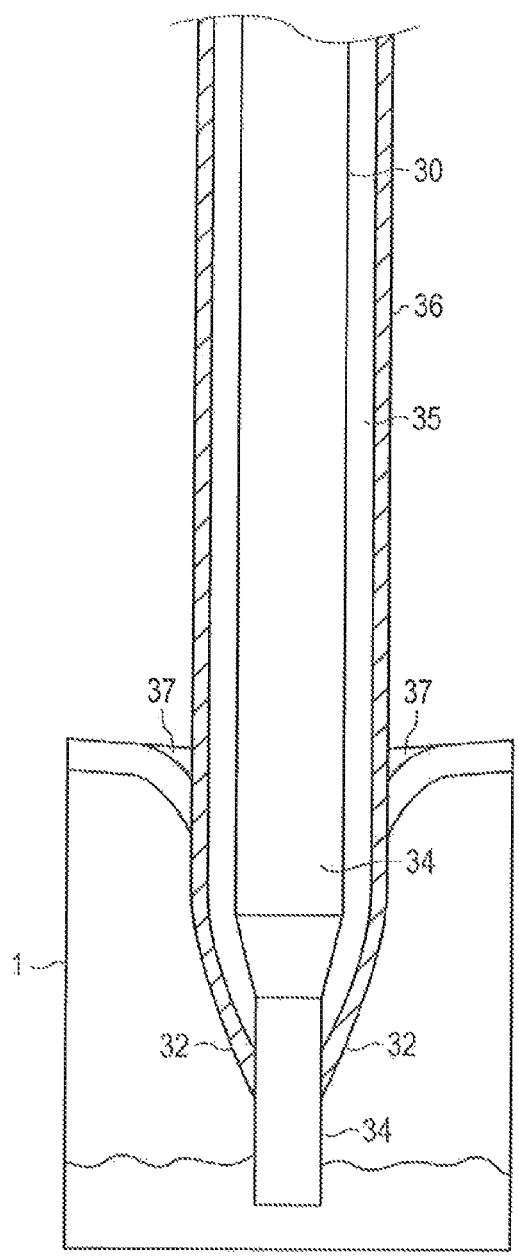
FIG. 6 depicts a partial cut-away side view of the distal portion of an exemplary sample probe according to the invention, housed within the lumen of the distal portion of an exemplary piercing probe of an exemplary sampling assembly of the invention.

FIG. 6 illustrates a partial cut away side view of the distal portion of an exemplary sample probe 30, housed within the lumen 35 of the distal portion of an exemplary piercing probe 36 of a sampling assembly 3 according to one embodiment of the invention. As shown in FIG. 6, according to one embodiment of the invention, when the sample probe 30 is positioned in the sample vial 7, the piercing probe 36 encloses the sample probe 30 to prevent the sample probe 30 from contacting the seal 37 of the sample vial 7. The barrier formed by the piercing probe 36 prevents pieces of the frangible seal 37 from partially or completely clogging or blocking the opening of the sample probe lumen 33 at the tip 34 of the sample probe 30. Furthermore, because the sample probe 30 never touches the seal 37 of the sample vial 7, the surface area of the sample probe 30 that would otherwise require cleaning is minimized thereby decreasing wash time and quantity of wash fluids required, thereby improving the overall efficiency of the analyzer 10.

In addition, in one embodiment according to the invention, the lumen 35 of the piercing probe 36 acts as a vent for the sample tube 7. Venting of the sample tube 7 is advantageous because venting equalizes the pressure inside the sample tube 7 with the pressure outside the sample tube 7 to ensure the accuracy of aspiration volumes. By eliminating venting ports on the piercing probe 36 that would otherwise be required to permit venting, the likelihood that fragments of the seal 37 will clog the piercing probe 36 is minimized. Reduced sample probe 30 clogging allows for greater sampling accuracy and reduce the possibility of damage to the sample probe 30, in particular, the sample probe tip 34. In addition, reduced clogging decreases the amount of time required to clean the sample probe 30 and the piercing probe 36, thereby improving the overall efficiency of the sample analyzer 10.

Figure 7:
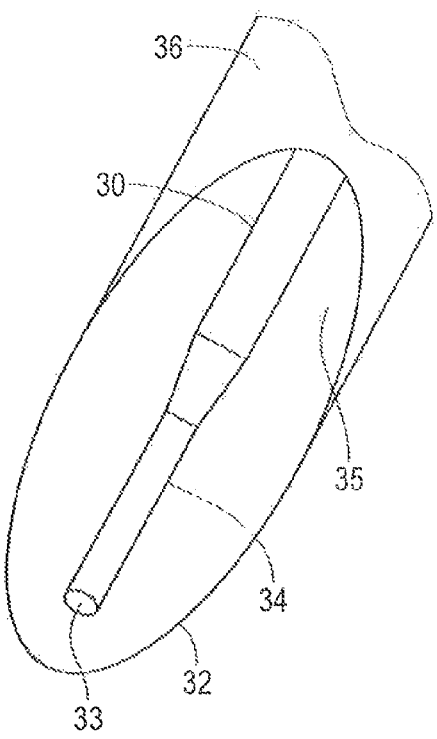
FIG. 7 shows a perspective view of the distal portion of an exemplary sample probe housed within the lumen of the distal end and extended beyond the opening of an exemplary piercing probe according to the invention.

FIG. 7 shows a perspective view of the distal portion of an exemplary sample probe 30 housed within the lumen 35 of the distal portion of an exemplary piercing probe 36 according to the invention. The tip 34 of the sample probe 30, illustrated in FIG. 7, is exposed in the opening of the lumen 35 at the distal tip 32 of the piercing probe 36.

Figure 8:
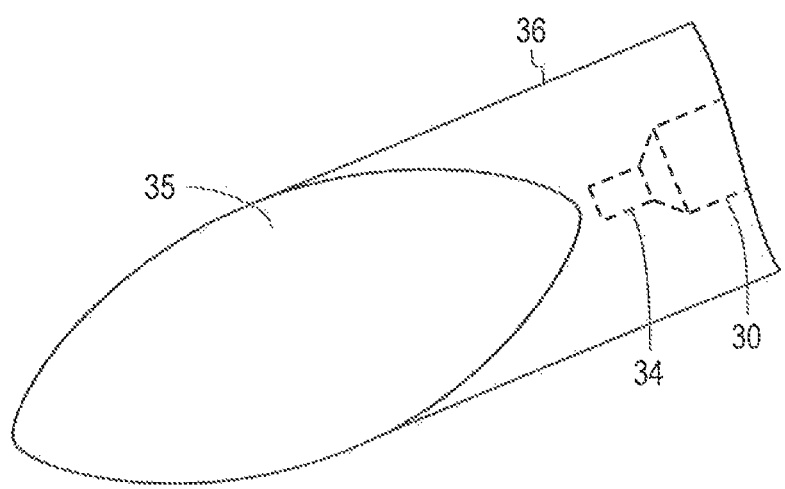
FIG. 8 shows a perspective view of the distal portion of an exemplary sample probe housed and completely enclosed within the lumen of the distal end of an exemplary piercing probe according to the invention wherein the distal portion of the sample probe is enclosed.

FIG. 8 shows another perspective view of the exemplary sample probe 30 housed within the lumen 35 of an exemplary piercing probe 36 of the invention. As shown in FIG. 8, the tip 34 of the sample probe 30 (shown in outline) is withdrawn proximally into the lumen 35 of the piercing probe 36 where it is enclosed by the distal portion of the piercing probe 36 and is not exposed in the opening of the lumen 35 of the distal tip 32 of the piercing probe 36. The sample probe 30 and the piercing probe 36 are axially slideably moveable relative to one another. For example, by withdrawing the piercing probe 36 proximally, and maintaining the sample probe 30 stationary, the distal tip 34 of the sample probe 30 is positioned, i.e., exposed in the opening of the lumen 35 of the distal tip 32 of the piercing probe 36. Alternatively, the sample probe 30 is advanced distally while the piercing probe 36 remains stationary. In yet another embodiment of the invention, both the sample probe 30 and the piercing probe 36 are slideably moveable. Because of the relative movement of the sample probe 30 and the piercing probe 36, when the piercing probe 36 punctures the seal 37 on the sample tube 7, the distal tip 34 of the sample probe 30 is positioned i.e., enclosed within the lumen 35 of the piercing probe 36 and not extended beyond the tip 32 of the piercing probe 36, as shown in FIG. 8. When ready to aspirate the sample from the sample tube 7, the distal tip 34 of the sample probe 30 is positioned below, i.e., extended beyond the piercing probe tip 32, as shown in FIG. 6, positioned within or within the opening of the lumen 35 of the tip 32 of the piercing probe 36. While the tip 32 of the piercing probe 36 may encounter sample during the process of piercing the seal 37, portions of the piercing probe 36 proximal to the tip 32 are not immersed in sample. By minimizing the surface area of the piercing probe 36 that is exposed to sample, the surface area of the piercing probe 36 that requires cleaning is reduced.

Figure 9A:
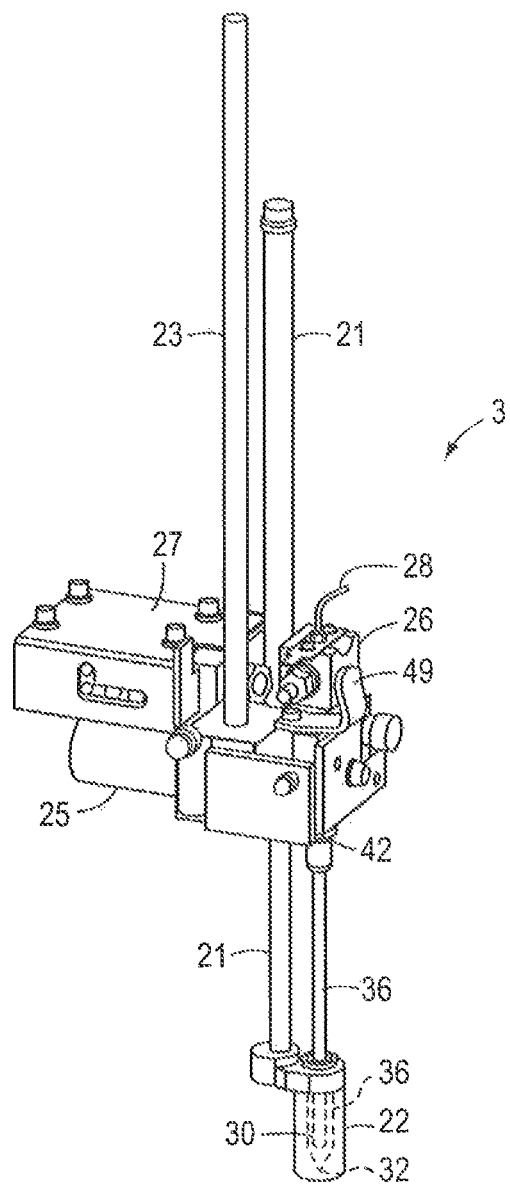
FIG. 9A is a perspective view of a sampling assembly including an exemplary closed-tube piercing probe and sample probe of the invention in an unreleased position.
Figure 9B:
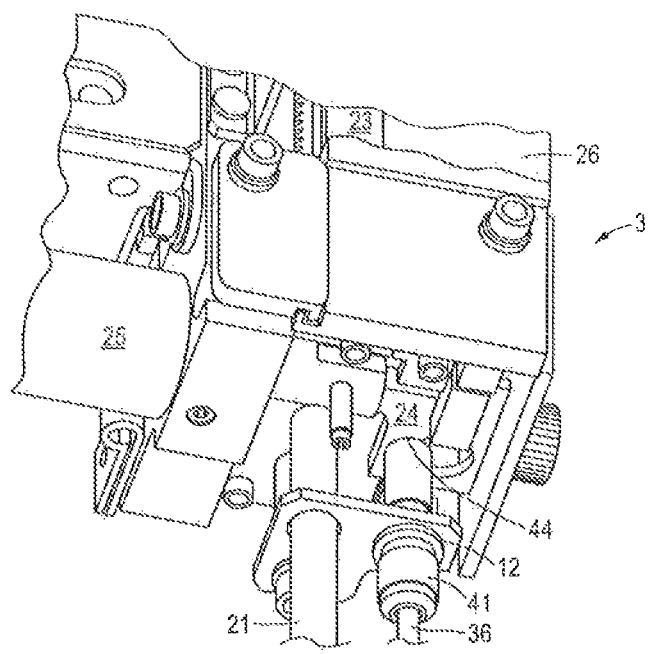
FIG. 9B is a perspective view of the proximal portion of sampling assembly including the exemplary closed-tube piercing probe and sample probe assembly of FIG. 9A.

FIG. 9A is a perspective view of an exemplary closed-tube piercing probe and sample probe assembly of the invention in an unreleased position. FIG. 9B is a perspective view of the proximal portion of the exemplary closed-tube piercing probe and sample probe assembly of FIG. 9A. In the unreleased position shown in FIG. 9A, both the tip 32 of the piercing probe 36, and the tip 34 of the sample probe 30 are enclosed. The tip 32 of the piercing probe 36 is covered by the foot 22 and tip 34 of the sample probe 30 is housed within the piercing probe 36.

With continued reference to FIG. 9A, the foot 22 has a lumen (best illustrated in FIG. 2B) through which the piercing probe 36 housing the sample probe 30 pass. According to one embodiment of the invention, the foot 22 is coupled to a brake rod 21. The brake rod 21 and the foot 22 move independently of the other elements of the sampling assembly 3 and hold the sample tube 7 in place while the sampling cycle occurs. In a further embodiment, the brake rod 21 may be attached to the positioning arm 1.

With continued reference to FIG. 9A and FIG. 9B, according to one embodiment of the invention, the sampling assembly 3 includes a seal assembly 26 that engages the proximal end 41 (See FIG. 3) of the piercing probe 36, scaling the proximal end 41 from the external environment. In one embodiment, the seal assembly 26 provides an orifice 49 for the introduction of fluids or gases for cleaning the lumen 35 of the piercing probe 36. In one embodiment, the proximal end 28 of the sample probe 30 serves as an entrance point 28 for the introduction of fluids or gases that may be used, for example, to clean the lumen of the sample probe 30.

Referring back to FIG. 1 according to one embodiment, the proximal end 41 of the piercing probe 36 of the sampling assembly 3 sealingly joins to a length of tubing 80. The tubing 80 may be formed of a polymer, such as Tygon™. The tubing 80 connects the proximal end 41 of the piercing probe 36 at the orifice 49 of the seal assembly 26 so as to be in fluid communication with the positive pressure gas source 70. The tubing 80 may be in the form of a single length of tubing, or in multiple lengths of tubing sealingly joined by additional orifices, gaskets, valves, or other sealable junctions.

With continued reference to FIG. 1, in certain embodiments, the sample collecting device 18 includes an accumulator 62 to contain pressurized air or other gaseous fluid. The accumulator 62 is sealingly joined, through a length of tubing 80, to the sampling assembly 3 on one end and to the positive pressure gas source 70 on the other end. The accumulator 62 is a container capable of containing a volume of pressurized gas and maintaining the pressurized gas at a desired magnitude of positive pressure. According to one embodiment of the invention, the accumulator 62 is capable of containing a volume of gas in the range of about 200 cc to 500 cc, most preferably 300 cc.

With continued reference to FIG. 1, according to one embodiment of the invention, the positive pressure gas source 70 is, for example, a positive pressure gas pump, capable of generating pressurized gas. According to an alternative embodiment, pressurized gas is provided to the sample collecting device 18 through a remote positive pressure gas source, such as a centralized "in house" pressurized gas line, in fluid communication with the lumen 35 of the piercing probe. In one embodiment, the positive pressure gas source 70 is provided with or without an accumulator 62.

In another embodiment of the invention, referring still to FIG. 1, the accumulator 62 includes a gas pressure meter 66 and/or a gas pressure sensor 72. The exemplary gas pressure meter 66 provides a visual display of the current gas pressure within the accumulator 62. The gas pressure sensor 72 measures the gas pressure within the accumulator 62 and provides a signal to the positive pressure gas source 70, for example, a positive pressure air pump. When the gas pressure in the accumulator 62 falls below the desired gas pressure magnitude, the sensor 72 signals the gas source 70 to switch on and to increase the gas pressure within the accumulator 62. Once the gas pressure sensor 72 measures a gas pressure at the desired magnitude, the sensor 72 signals the gas source 70 to switch off. The combination of the sensor 72 and the gas source 70 maintains a near constant desired gas pressure within the accumulator 62. According to one embodiment of the invention, the gas pressure within the accumulator 62 is preferably in a range from about 25 PSIA to 30 PSIA, more preferably from about 27 PSIA to 28 PSIA, and preferably 27 PSIA.

Referring still to FIG. 1, according to one embodiment of the invention, the sample collecting device 18 includes a valve 40. The valve 40 reversibly alternates between an open position and a closed position through the movement of a switch 42. When the valve 40 is in the open position, the lumen 35 of the piercing tube 36 is in communication with the valve 40, and the tubing 80 between the free end 32 of the piercing tube 36 and the accumulator 62. When the valve 40 is in the closed position, the gas pressure in the lumen 35 between the valve 40 and the tip 32 of the piercing tube 36 maintains a first gas pressure, equal to atmospheric pressure at the free end 32 of the piercing tube 36. When the valve 40 is in the closed position, the gas pressure present between the valve 40 in the lumen 31 of the tubing 80 to the accumulator 62 maintains a second gas pressure, equal to the gas pressure generated by the positive pressure gas source 70.

Figure 10:
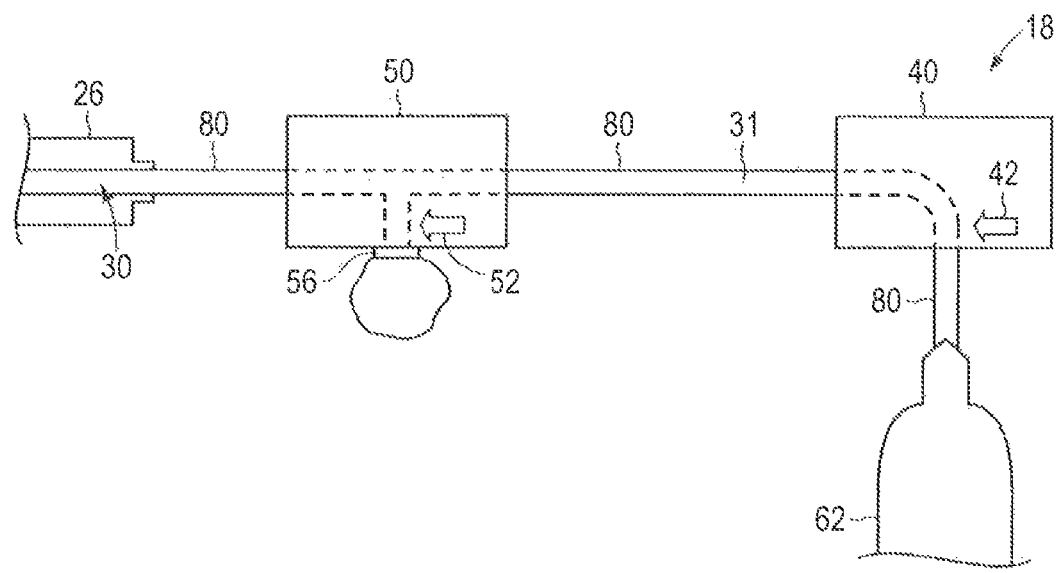
FIG. 10 is a schematic view of a portion of the sample collecting device in FIG. 1 including a first valve and a second valve according to an illustrative embodiment of the invention.

Referring now to FIG. 10, the sample collecting device 18, according to an alternative embodiment, includes a first valve 40 and a second valve 50. According to this embodiment, the first valve 40, a two-way valve, opens and closes a fluid communication between the lumen 31 of the gas tubing 80 and the pressurized gas within the accumulator 62. The second valve 50, a three-way valve, opens and closes a fluid communication between the lumen 31 of the gas tubing 80 and an orifice 56 open to room air at atmospheric pressure. Accordingly, in the closed position, the orifice 56 of the second valve 50 is no longer patent (open), i.e., it is closed. When the first valve 40 is in the closed position and the second valve 50 is in the closed position, the pressure in the lumen 31 is equal to atmospheric pressure, i.e., the gas pressure at the only orifice that is open, the open end 32 of the piercing tube 36 (shown in FIG. 1).

With continued reference to FIG. 10, when the first valve 40 is in the open position and the second valve 50 is in the closed position, the pressure within the lumen 31 between the second valve 50 and the accumulator 62 equals the pressure of the gas pressure contained within the accumulator 62. When the first valve 40 is initially opened, the lumen 31 experiences a sudden burst of positively pressurized gas. As the first valve 40 remains open, the pressure of the gas decreases until the entire system, including the lumen 31 and the open gas accumulator 62, equalize towards the gas pressure at the open end 32 of the piercing tube 36 (shown in FIG. 1). According to one embodiment of the invention, the first valve 40 is only opened for a few milliseconds, permitting a short blast of positively pressured gas to escape and to purge the lumen 35 of the piercing tube 36 and to dry the outside tip of the piercing tube 36, but maintaining sufficient gas pressure within the accumulator 62 for subsequent blast cycles without requiring substantial recharging of positive pressure by the gas source 70. According to one embodiment of the invention, the first valve 40 is opened from 10 milliseconds to 4 seconds; more preferably 30 milliseconds to 2 seconds; and most preferably 50 milliseconds to 1 second.

Referring still to FIG. 10, when the first valve 40 is in the closed position and the second valve 50 is in the open position, the gas within the lumen 31 of the tubing 80 and the piercing tube 36 (not shown) is at a gas pressure equal to atmospheric pressure. Referring again to FIG. 1, when the free end 32 of the piercing tube 36 is outside the sample tube 7, the pressure within the lumen 35 of the piercing tube 36 is equal to atmospheric pressure. Alternatively, when the free end 32 of the piercing tube 36 is extended into the sample tube 7, the pressure within the lumen 35 of the piercing tube 36 will equilibrate with the pressure, either positive or negative, of the sample tube 7. For example, if the sample tube 7 is sealed with a sample tube cap 37, the sample tube 7 may have an internal gas pressure either higher or lower than atmospheric pressure. Additionally, aspiration of a sample from the sample tube 7 by the sample probe 30 may lower the gas pressure within the sample tube 7, and subsequently within the lumen 35 of the piercing tube 36, to a gas pressure below atmospheric pressure. In this situation, the pressure within the free end 32 of the piercing tube 36 will equilibrate with atmospheric pressure, by venting through the open orifice 56 of the second valve 50.

Gas pressures remaining in the sampling assembly either above or below atmospheric pressure may introduce errors in the amount of sample aspirated. For example, an automated aspirating probe may be programmed to aspirate sample for a predetermined period of time or for a predetermined volume, such that a standardized sample volume is aspirated during each procedure. If the sample is aspirated at a gas pressure either above or below atmospheric pressure, a timed sample aspiration may result in either too much or too little sample being aspirated, introducing errors into subsequent analyses. A vent to atmospheric pressure reduces the likelihood that such a sampling error will occur.

Figure 11:
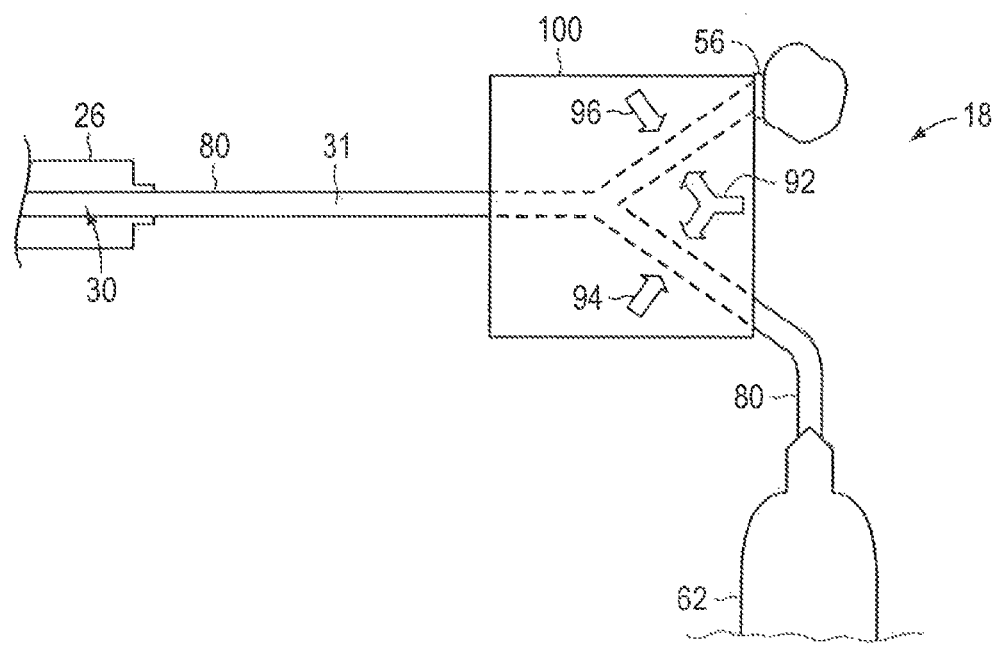
FIG. 11 is a schematic view of a portion of the sample collecting device in FIG. 1 including a valve according to another illustrative embodiment of the invention.

Now referring to FIG. 11, in an alternative embodiment, the sample collecting device 18 includes a single three-way valve 100 connecting the lumen 35 of the piercing tube 36 (not shown) to the accumulator 62 and also to an orifice 56 open to room air at atmospheric pressure. According to one embodiment of this invention, the three-way valve 100 includes a single toggle switch 92 alternating fluid communication between the lumen 35 of the piercing tube 36 and either the accumulator 62 or the atmosphere. According to an alternative embodiment, the valve 100 includes two toggle switches 94, 96 allowing three states of fluid communication. When both switches 94, 96 are in their closed positions, the lumen 35 of the piercing tube 36 (not shown) is only open at its free end 32 and the gas pressure within the lumen 35 tends toward (atmospheric pressure,) the gas pressure at the free end 32. When the first switch 94 is in its closed position and the second switch 96 is in its open position, the gas pressure in the lumen 31 tends toward atmospheric pressure. When the first switch 94 is in its open position and the second switch 96 is in its closed position, the lumen 35 is exposed to the pressurized gas stored in and released from the accumulator 62. It is contemplated that alternative valve schematics, including at least one three-way valve or at least two two-way valves combinations of two-way and three-way valves, may be utilized that allow alternation between the at least two desired states.

Figure 12:
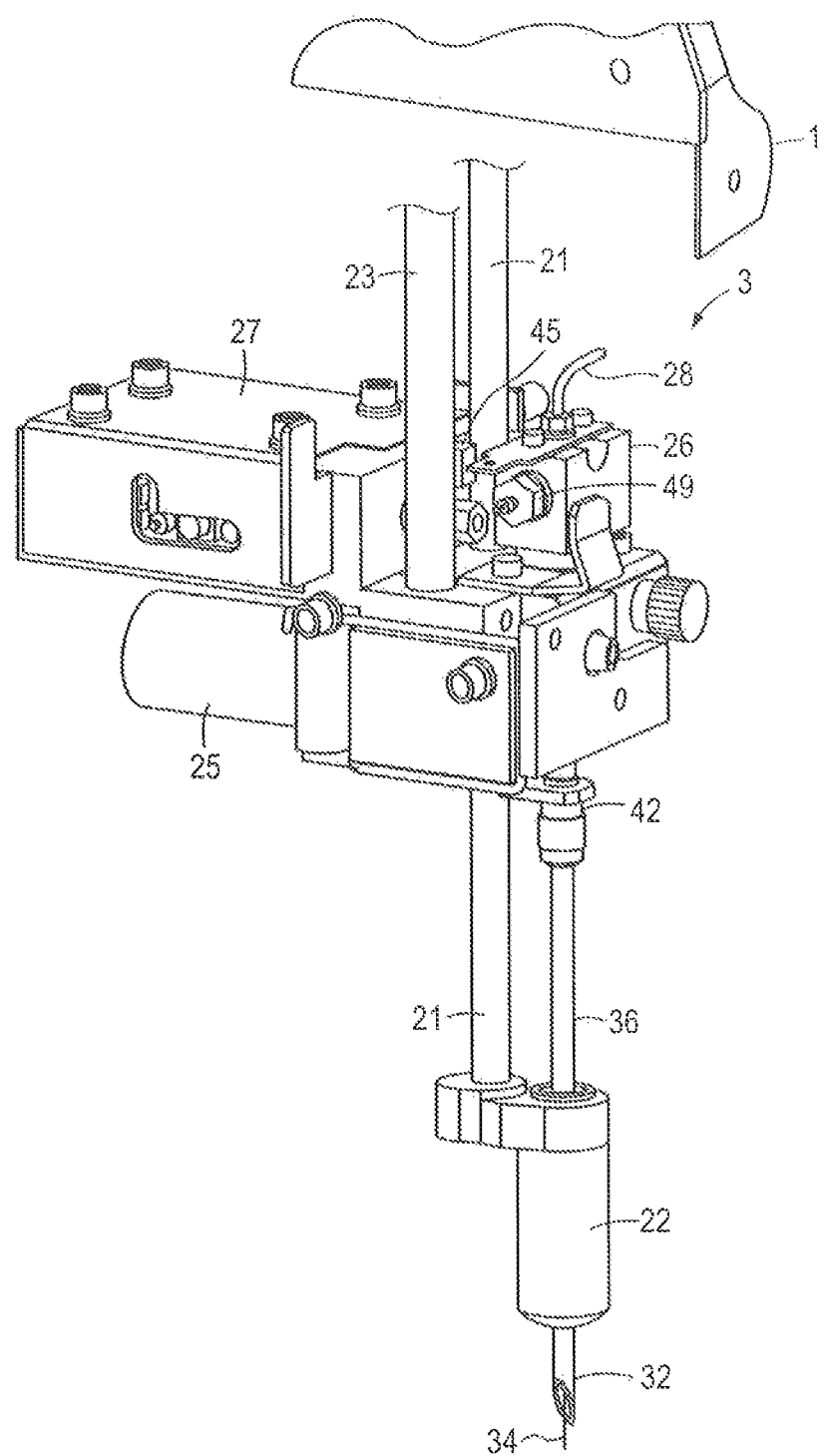
FIG. 12 is a perspective view of an exemplary closed-tube piercing probe and sample probe assembly sampling assembly of the invention wherein the tip of the piercing probe and the tip of the sample probe are exposed.

Referring now to FIG. 12, in one embodiment according to the invention, the sampling assembly 3 includes a solenoid 25 which controls a lock 24 for engaging the upper detent 44 or the lower detent 42 of the piercing probe 36.

In one embodiment according to the invention, the sample probe 30 is coupled to the sampling assembly 3 via the seal assembly 26. Vertical movement of the piercing probe 36 is necessary to expose or enclose, i.e., cover the distal end 34 of the sample probe 30. When the lock 24 engages the upper detent 44, the piercing probe 36 is locked in lowered position such that the tip 34 of the sample probe 30 is enclosed within the lumen 35 of the piercing probe 36 and is not exposed. If the lock 24 engages the lower detent 42, the piercing probe 36 is locked in a raised position, exposing the distal end 34 of the sample probe 30. Thus, in one embodiment, the sample probe 30 remains in a constantly fixed position relative to the sampling assembly 3, while the piercing probe 36 moves relative to the sample probe 30 and the sampling assembly 3. However, in another embodiment, the sample probe 30 may alternatively be designed to move relative to a piercing probe 36 fixed in a constant position relative to the sampling assembly 3. In a further embodiment, neither the sample probe 30 nor the piercing probe 36 are fixed, but both are capable of movement relative to the other and relative to the sampling assembly 3.

With continued reference to FIG. 12, in one embodiment of the invention, the sampling assembly 3 includes an information processing unit 8, such as, for example, a PC board, controller or digital signal processor, which sends to and receives information from various sensors 45 associated with the sampling assembly 3. The information processing unit 8 also controls a solenoid 25 which operates to release or engage the lock 24. In addition, in one embodiment according to the invention, the information processing unit 8 communicates with a main computer (not shown) operating the analyzer.

With continued reference to FIG. 12, the sampling assembly 3 is attached to the positioning arm 1 by a z-rack 23, according to one embodiment of the invention. A motor (not shown) on the positioning arm 1 drives the z-rack 23 up and down in the z-axis (vertical), thus moving the sampling assembly 3 up and down in the z-axis, thereby moving the sample probe 30 and the piercing probe 36 upwards or downwards, piercing the cap 37 of the sample tube by the piercing probe 36 and sampling the patient fluid in the vial 7 by the sample probe 30. In one embodiment according to the invention, the sample probe 30 and/or the piercing probe 36 is in communication with a sensor (not shown) that detects contact of the sensor probe 30 with a fluid or a solid. As used throughout the specification, the term sensor includes optical, mechanical, or electromechanical sensors, for example. A sensor may also be a circuit that detects a shift in capacitance. For example, a sensor may detect motion parallel to the length of the sample probe 30 or piercing probe 36 to move the apparatus to detect the head of shoulder screws to determine the coordinates of target locations. The same motion may be used to detect fluid in tubes, cups or the cuvette. Alternatively, motion normal to the length of the probes may be used. In yet another embodiment, the sampling probe 30 and the piercing probe 36 are joined by, for example, a circuit, connector or cable to detect motion between the sample probe 30 and piercing probe 36 to ensure motion between the probes does not cause false detection of fluid thereby to eliminate false liquid level detection.

In one aspect, the invention is a method for automated sampling of patient fluid by the clinical diagnostic analyzer including a sample collecting device. In order to obtain the sample from a sample tube 7 containing the patient sample, the seal 37 of the sample tube 7 must first be pierced by the tip 32 of the piercing probe 36. Before piercing the seal 37, the sample probe 30 is locked in a retracted position to prevent damage to the sample probe while the seal 37 is pierced.

Referring to FIGS. 9A and 9B, in a first position, the upper detent 44 of the piercing probe 36 is engaged by the lock 24. This positions the sample probe 30 in a retracted position relative to the piercing probe 36, for example as shown in FIG. 9A, such that the tip 34 of the sample probe 30 is enclosed by the piercing probe 36 and will not be exposed or damaged during the seal 37 piercing step.

With continued reference to FIG. 9A, in order for the piercing probe 36 to pierce the seal 37 of a sample tube 7, the foot 22 first contacts the seal 37. When the foot 22 contacts the top of a sample tube 7, the brake rod 21 moves upward in the z-axis, releasing a flag from the sensor 47. This causes the z-rack 23 to drive downward and moves the piercing probe 36 through the lumen of the foot 22 to perforate the seal 37 of the tube 7. In one embodiment of the invention, the piercing probe 36 may be spring-loaded to permit movement of the piercing probe 36 upward when sampling from uncapped sample tubes 7. When accessing samples in capped tubes 7, once the piercing probe 36 enters the cap 37, friction prevents the spring from releasing and moving the piercing probe 36 upwards. Therefore, once the seal is broken, the z-rack 23 drives upward, allowing the lock 24 to release and the spring (not shown) to expand, moving the piercing probe 36 upward to expose the sample probe 30 housed within. During this step, the tip 32 of the piercing probe 36 remains in the sample tube 7. The lock 24 then reengages the piercing probe 36 in the lower detent 42. The z-rack 23 subsequently drives the sampling assembly 3 downward so that the tip 34 of the sample probe 30 can aspirate the sample in the tube 7. The z-rack 23 then drives upward allowing the sample probe 30 and piercing probe 36 to exit the sample tube 7 simultaneously. The foot 22 strips the sample tube 7 from the piercing probe 36 as the piercing probe 36 is driven upward by the z-rack 23.

Referring back to FIG. 2A, the sampling assembly 3 then moves to another location of the analyzer 10 to release the sample into a cuvette 108. To move in the x-axis and y-axis, the sampling assembly travels along the z-axis of the positioning arm 1, while the positioning arm 1 moves simultaneously along the x-axis of the rail 5.

With reference to FIG. 2B, in one embodiment according to the invention, the wash station 9 includes a deep washer for deep washing the distal portion 34 of the sample probe 30 and the distal portion 32 of the piercing probe 36. The deep washer includes a radial rinser for 180 rinsing the exterior of the piercing probe 36, the interior of the piercing probe 36 tip 32 and the exterior of the sample probe 30 tip 34. The radial rinser is attached to a radial rinse pump (not shown) which is activated when the piercing probe is brought up in the z-axis. The radial rinser 180 sprays a radial shower of rinse solution through a plurality of radially arranged rinse ports 182. The deep washer 9 may further feature an internal sample probe rinser.

The lumen 33 of the sample probe 30 is washed by a stream of rinse fluid passed through the lumen 33 of the sample probe 30 in fluid communication with a sample probe rinser pump. The flow rate of rinse fluid through the lumen 33 of the sample probe 30 is in the range of about 0.25 to 2.0 ml/second, preferably about 1.0 to 1.5 ml/second, more preferably 1.05 ml/sec.

In a further embodiment, an air pump or gas source 70 such as, for example, the gas source 70 described above with respect to the venting mechanism, is joined in fluid communication with the lumen 35 of the piercing probe 36. The pressurized gas from the gas source 70 purges residual fluid from the annular area between the sample probe 30 and the piercing probe 36 after a deep wash cycle. The gas source 70 is required to maintain a clear vent path needed during aspiration in the closed tube system described herein. Without a clear vent path, the internal pressure of the sample tube will not be at atmospheric pressure. A partial tube pressure above atmospheric leads to over aspiration; a partial vacuum leads to under aspiration. A clear vent path allows the immediate pressure equalization inside the sample tube and maintains good precision and accuracy for sampling.

In a further embodiment according to the invention, the gas source 70 is an air purge system such as a jet including a tube 160 with an opening positioned adjacent the piercing probe tip that supplies a short burst of air through an orifice in the foot 22 to the outside of the piercing probe tip. The short burst of air removes any residual rinse fluid that may remain on the piercing probe tip after the deep wash.

In another embodiment, the deep washer 9 includes a replaceable filter 184 for removing debris following piercing of the sample tube seal by the piercing probe 36. The debris is material displaced from the tube cap generated during the piercing process. The filter prevents the debris from blocking tubing to and from the washer. The filter is replaceable by laboratory personnel avoiding costly service calls. Typically, the filter is replaced every 5000 cycles. A verification system such as a sensor may be installed to verify the filter is in place.

At least one advantage of the sample collecting device 3 according to the invention is that the sample tube 7 is pierced by the piercing probe 36 and the sample fluid is aspirated by the sample probe 30 without the need for the sampling assembly 3 to move in the x-axis or the y-axis. This feature reduces the time required to obtain a sample aliquot from the sample tube 7 and improves throughput time, thus increasing the efficiency of the sample analyzer 10. For example, the table below

|   | PT (tests per hour) | APTT (tests per hour) |
|---|---|---|
| A | 270 | 270 |
| B | 228 | 120 | compares the actual throughput of a sample collecting device according to the invention (A) for prothrombin time (PT) and activated partial thromboplastin time (APTT) to the actual throughput of a pre-existing sample collecting device (B) for the same tests. The sample collecting device according to the invention processes 270 PT tests/hour and 270 APTT tests per hour while the pre-existing sample collecting device processes 228 PT and 120 APTT tests per hour. Thus, the throughput of the sample collecting device according to the invention is more than double the throughput of the pre-existing sample collecting device.

Furthermore, because the tip 32 of the piercing probe 36 is positioned within the sample tube 7 from the initial pierce until the sample is aspirated, the likelihood of contamination that would otherwise result from multiple entries into the sample tube 7 is reduced.

Other advantages of the sampling assembly 3 according to the invention described herein include the ability of the sample analyzer 10 utilizing the sampling assembly 3 of the invention to process a batch of sample tubes 7 where some tubes 7 are capped or sealed and some tubes 7 lack caps or seals. This is possible because the piercing probe 36 and the sample probe 30 can perform the same steps on a sample tube, regardless of whether a cap is present.

Furthermore, the telescoping configuration of the sample probe 30 and the piercing probe 36 eliminates the need for movement in the x-axis or y-axis during the piercing and sampling stage enabling the sampling assembly 3 to be more easily centered on a sample tube cap 37. Accordingly, the sampling assembly 3 samples from sample tubes 7 of differing diameters and geometries, as well as samples from sample tube caps or seals 37 of differing diameters and materials. Furthermore, the ability of the sampling assembly 3 to move in the z-axis, allows the sampling assembly 3 to sample from tubes 7 of different heights in the same batch. Thus, any variety of sample vials may be placed in the sample tube receiving area 102 (see, e.g., FIG. 2A).

While the sampling assembly including the venting mechanism described herein is preferably used in aspirating a patient sample, the sampling assembly is also useful for aspirating volumes of other fluids or liquids, including reagents, for example. These fluids may be aspirated from any number of containers including, but not limited to vials, test tubes, and sample tubes. Other variations, modifications, and implementations of what is described herein will occur to those of ordinary skill in the art without departing from the spirit and the scope of the invention as claimed. Accordingly the invention is not to be defined by the preceding illustrative description, but instead by the spirit and scope of the claims that follow.

What is claimed is:

1. A method for analyzing a sample in a sample container, comprising:
   (i) providing a sample collecting device comprising a sampling assembly comprising,
      (a) a first tube comprising a lumen and an upper detent and a lower detent;
      (b) a locking mechanism,
      (c) a second tube comprising a lumen and a free end, wherein said second tube is enclosed within the lumen of said first tube; and,
      (d) a system for moving said first tube and said second tube relative to each other in a vertical axis comprising,
         a z-rack operatively joined to said first and second tubes,
         one or more motion sensors for detecting motion parallel to the length of at least one of the first tube or the second tube and a foot assembly wherein said one or more motion sensors is engaged by said foot assembly to determine when said container is in a position for piercing, and
         a motor operatively connected to said z-rack for driving said z-rack;
   (ii) reversibly engaging said locking mechanism with said lower detent of said first tube;
   (iii) contacting said foot assembly with said sample container;
   (iv) driving said Z-rack vertically via said motor and in response to said sensors, moving said first tube in a vertical axis from a first position to a second position into said sample container and piercing a seal of said sample container;
   (v) axially moving the free end of said second tube from an enclosed position within the lumen of the first tube to a deployed position;
   (vi) collecting the sample from the sample container with the free end of the second tube, wherein said second tube is operatively joined to a pump;
   (vii) providing an analysis station in communication with said second tube; and,
   (viii) analyzing said sample.

2. The method of claim 1 further comprising transporting said sample by the second tube via a proximal end connectable to a supply member that serves as a conduit to transport said sample by the second tube.

3. The method of claim 1 further comprising venting the sample container by the lumen of the first tube.

4. The method of claim 3 wherein said venting equalizes inside pressure of the sample container with outside pressure of the sample container.

5. The method of claim 1, wherein said sample is a patient fluid.

6. The method of claim 1 wherein during said collecting step the free end of the second tube transitions from an enclosed position within the lumen of the first tube to a deployed position beyond a pointed tip of the first tube.

7. The method of claim 1 wherein prior to said collecting step said second tube is locked in a retracted position by said locking mechanism.

8. The method of claim 1 wherein said upper and said lower detents position the first tube relative to the second tube.

9. The method of claim 1 wherein the first tube is locked in lowered position such that a pointed tip of the second tube is enclosed within the lumen of the first tube while the lock engages the upper detent.

10. The method of claim 1 wherein while the lock engages the lower detent, the first tube is locked in a raised position, exposing a distal end of the second tube.

11. The method of claim 1 wherein the second tube remains in a constantly fixed position relative to the sampling assembly, while the first tube moves relative to the second tube and the sampling assembly.

12. The method of claim 1 wherein the first tube remains in a constantly fixed position relative to the sampling assembly while the second tube moves relative to the first tube and the sampling assembly.

13. The method of claim 1 wherein the first tube and the second tube move relative to each other and relative to the sampling assembly.

* * * * *